(12) United States Patent
Trautwein et al.

(10) Patent No.: US 8,470,001 B2
(45) Date of Patent: Jun. 25, 2013

(54) POLYAXIAL SCREW

(75) Inventors: Frank T. Trautwein, Filderstadt (DE); Gary L. Lowery, Jacksonville, FL (US)

(73) Assignee: Paradigm Spine, LLC, New York, NY (US)

( * ) Notice: Subject to any disclaimer, the term of this patent is extended or adjusted under 35 U.S.C. 154(b) by 16 days.

(21) Appl. No.: 13/088,741

(22) Filed: Apr. 18, 2011

(65) Prior Publication Data

US 2011/0196427 A1 Aug. 11, 2011

Related U.S. Application Data

(63) Continuation of application No. 11/538,524, filed on Oct. 4, 2006, now Pat. No. 7,927,359.

(60) Provisional application No. 60/724,046, filed on Oct. 6, 2005.

(51) Int. Cl.
*A61B 17/70* (2006.01)
(52) U.S. Cl.
USPC ............ 606/264; 606/265; 606/266; 606/300
(58) Field of Classification Search
USPC .................................. 606/246–279, 300–321
See application file for complete search history.

(56) References Cited

U.S. PATENT DOCUMENTS

| | | |
|---|---|---|
| 4,887,596 A | 12/1989 | Sherman |
| 4,946,458 A | 8/1990 | Harms et al. |
| 5,176,678 A | 1/1993 | Tsou |
| 5,207,678 A | 5/1993 | Harms et al. |
| 5,261,909 A | 11/1993 | Sutterlin et al. |
| 5,261,910 A | 11/1993 | Warden et al. |
| 5,304,179 A | 4/1994 | Wagner |
| 5,395,371 A | 3/1995 | Miller et al. |
| 5,413,576 A | 5/1995 | Rivard |
| 5,466,237 A | 11/1995 | Byrd, III et al. |
| 5,486,174 A | 1/1996 | Fournet-Fayard et al. |
| 5,499,983 A | 3/1996 | Hughes |

(Continued)

FOREIGN PATENT DOCUMENTS

| | | |
|---|---|---|
| FR | 2730405 | 8/1996 |
| JP | 11347046 | 12/1999 |

(Continued)

OTHER PUBLICATIONS

Office Action for corresponding Japanese Appl. No. 2008-534692 dated Sep. 6, 2011.

(Continued)

*Primary Examiner* — Eduardo C Robert
*Assistant Examiner* — Christina Negrellirodriguez
(74) *Attorney, Agent, or Firm* — Tram Anh Nguyen; Donald D. Min

(57) ABSTRACT

A bone-anchoring device is provided. The bone-anchoring device may comprise a screw including a threaded shaft portion configured to engage bone tissue, and a head portion having a cup-shaped cavity. The device may further include a rod connector and a linking member, wherein the linking member includes a spherical head portion configured to engage the cup-shaped cavity of the head of the screw, a widened flange s configured to engage the linking member, and an elongate body extending from the widened flange portion and configured to extend through an opening in the rod connector.

16 Claims, 8 Drawing Sheets

U.S. PATENT DOCUMENTS

| | | | |
|---|---|---|---|
| 5,501,684 A | 3/1996 | Schlapfer et al. |
| 5,540,690 A | 7/1996 | Miller et al. |
| 5,545,165 A | 8/1996 | Biedermann et al. |
| 5,549,608 A | 8/1996 | Errico et al. |
| 5,554,157 A | 9/1996 | Errico et al. |
| 5,569,247 A | 10/1996 | Morrison et al. |
| 5,578,034 A | 11/1996 | Estes |
| 5,584,834 A | 12/1996 | Errico et al. |
| 5,586,984 A | 12/1996 | Errico et al. |
| 5,591,166 A | 1/1997 | Bernhardt et al. |
| 5,628,740 A | 5/1997 | Mullane |
| 5,647,873 A | 7/1997 | Errico et al. |
| 5,669,911 A | 9/1997 | Errico et al. |
| 5,672,176 A | 9/1997 | Biedermann et al. |
| 5,690,630 A | 11/1997 | Errico et al. |
| 5,716,356 A | 2/1998 | Biedermann et al. |
| 5,725,527 A | 3/1998 | Biedermann et al. |
| 5,725,528 A | 3/1998 | Errico et al. |
| 5,728,098 A | 3/1998 | Sherman et al. |
| 5,733,285 A | 3/1998 | Errico et al. |
| 5,733,286 A | 3/1998 | Errico et al. |
| 5,735,850 A | 4/1998 | Baumgartner et al. |
| 5,735,851 A | 4/1998 | Errico et al. |
| 5,738,685 A | 4/1998 | Halm et al. |
| 5,752,957 A | 5/1998 | Ralph et al. |
| 5,797,911 A | 8/1998 | Sherman et al. |
| 5,800,435 A | 9/1998 | Errico et al. |
| 5,810,819 A | 9/1998 | Errico et al. |
| 5,817,094 A | 10/1998 | Errico et al. |
| 5,873,878 A | 2/1999 | Harms et al. |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,891,145 A | 4/1999 | Morrison et al. |
| 5,899,902 A | 5/1999 | Brown et al. |
| 5,954,722 A | 9/1999 | Bono |
| 5,954,725 A | 9/1999 | Sherman et al. |
| 5,984,924 A | 11/1999 | Asher et al. |
| 6,004,322 A | 12/1999 | Bernstein |
| 6,019,759 A | 2/2000 | Rogozinski |
| 6,053,917 A | 4/2000 | Sherman et al. |
| 6,074,393 A | 6/2000 | Sitoto |
| 6,077,262 A | 6/2000 | Schlapfer et al. |
| 6,083,227 A | 7/2000 | Saurat et al. |
| 6,132,434 A | 10/2000 | Sherman et al. |
| 6,183,472 B1 | 2/2001 | Lutz |
| 6,224,598 B1 | 5/2001 | Jackson |
| 6,261,287 B1 | 7/2001 | Metz-Stavenhagen |
| 6,280,442 B1 | 8/2001 | Barker et al. |
| 6,280,445 B1 | 8/2001 | Morrison et al. |
| 6,287,309 B1 | 9/2001 | Baccelli et al. |
| 6,287,311 B1 | 9/2001 | Sherman et al. |
| 6,309,391 B1 | 10/2001 | Crandall et al. |
| 6,379,354 B1 | 4/2002 | Rogozinski |
| 6,402,752 B2 | 6/2002 | Schaffler-Wachter et al. |
| 6,440,132 B1 | 8/2002 | Jackson |
| 6,451,021 B1 | 9/2002 | Ralph et al. |
| 6,454,769 B2 | 9/2002 | Wagner et al. |
| 6,471,705 B1 | 10/2002 | Biedermann et al. |
| 6,482,207 B1 | 11/2002 | Errico |
| 6,488,681 B2 | 12/2002 | Martin et al. |
| 6,554,831 B1 | 4/2003 | Rivard |
| 6,554,834 B1 | 4/2003 | Crozet et al. |
| 6,565,567 B1 | 5/2003 | Haider |
| 6,565,569 B1 | 5/2003 | Assaker et al. |
| 6,569,164 B1 | 5/2003 | Assaker et al. |
| 6,585,738 B1 | 7/2003 | Mangione et al. |
| 6,595,993 B2 | 7/2003 | Donno et al. |
| 6,626,908 B2 | 9/2003 | Cooper et al. |
| 6,641,586 B2 | 11/2003 | Varleur |
| 6,660,004 B2 | 12/2003 | Barker et al. |
| 6,663,632 B1 | 12/2003 | Frigg |
| 6,663,635 B2 | 12/2003 | Frigg et al. |
| 6,679,883 B2 | 1/2004 | Hawkes et al. |
| 6,716,214 B1 | 4/2004 | Jackson |
| 6,723,100 B2 | 4/2004 | Biedermann et al. |
| 6,726,687 B2 | 4/2004 | Jackson |
| 6,730,089 B2 | 5/2004 | Jackson |
| 6,733,502 B2 | 5/2004 | Altarac et al. |
| 6,736,816 B2 | 5/2004 | Ritland |
| 6,749,612 B1 | 6/2004 | Conchy et al. |
| 6,749,613 B1 | 6/2004 | Conchy et al. |
| 6,780,186 B2 | 8/2004 | Errico et al. |
| 6,827,719 B2 | 12/2004 | Ralph et al. |
| 6,835,196 B2 | 12/2004 | Biedermann et al. |
| 6,837,889 B2 | 1/2005 | Shluzas |
| 7,927,359 B2 | 4/2011 | Trautwein et al. |
| 2001/0034522 A1 | 10/2001 | Frigg |
| 2001/0047175 A1 | 11/2001 | Doubler et al. |
| 2002/0029040 A1 | 3/2002 | Morrison et al. |
| 2002/0035366 A1 | 3/2002 | Walder et al. |
| 2002/0077630 A1 | 6/2002 | Lin |
| 2002/0111628 A1 | 8/2002 | Ralph et al. |
| 2002/0120273 A1 | 8/2002 | Needham et al. |
| 2002/0183748 A1 | 12/2002 | Martin et al. |
| 2003/0004511 A1 | 1/2003 | Ferree |
| 2003/0004512 A1 | 1/2003 | Farris et al. |
| 2003/0023240 A1 | 1/2003 | Amrein et al. |
| 2003/0036758 A1 | 2/2003 | Frigg et al. |
| 2003/0050640 A1 | 3/2003 | Lee et al. |
| 2003/0100896 A1 | 5/2003 | Biedermann et al. |
| 2003/0158552 A1 | 8/2003 | Jeon et al. |
| 2003/0187439 A1 | 10/2003 | Biedermann et al. |
| 2004/0006342 A1 * | 1/2004 | Altarac et al. ............... 606/61 |
| 2004/0102781 A1 | 5/2004 | Jeon |
| 2004/0116929 A1 | 6/2004 | Barker et al. |
| 2004/0138660 A1 | 7/2004 | Serhan |
| 2004/0177847 A1 | 9/2004 | Foley et al. |
| 2004/0193157 A1 | 9/2004 | Falahee |
| 2004/0193160 A1 | 9/2004 | Richelsoph |
| 2004/0204711 A1 | 10/2004 | Jackson |
| 2004/0220570 A1 | 11/2004 | Frigg |
| 2004/0220575 A1 | 11/2004 | Biedermann et al. |
| 2004/0254574 A1 * | 12/2004 | Morrison et al. ............... 606/61 |
| 2004/0260284 A1 | 12/2004 | Parker |
| 2005/0192572 A1 | 9/2005 | Abdelgany et al. |

FOREIGN PATENT DOCUMENTS

| | | |
|---|---|---|
| JP | 2004507313 | 3/2004 |
| WO | 0217803 | 3/2002 |
| WO | 0224087 | 3/2002 |

OTHER PUBLICATIONS

Office Action for corresponding Taiwan Appl. No. 95137137 dated Sep. 18, 2012.

* cited by examiner

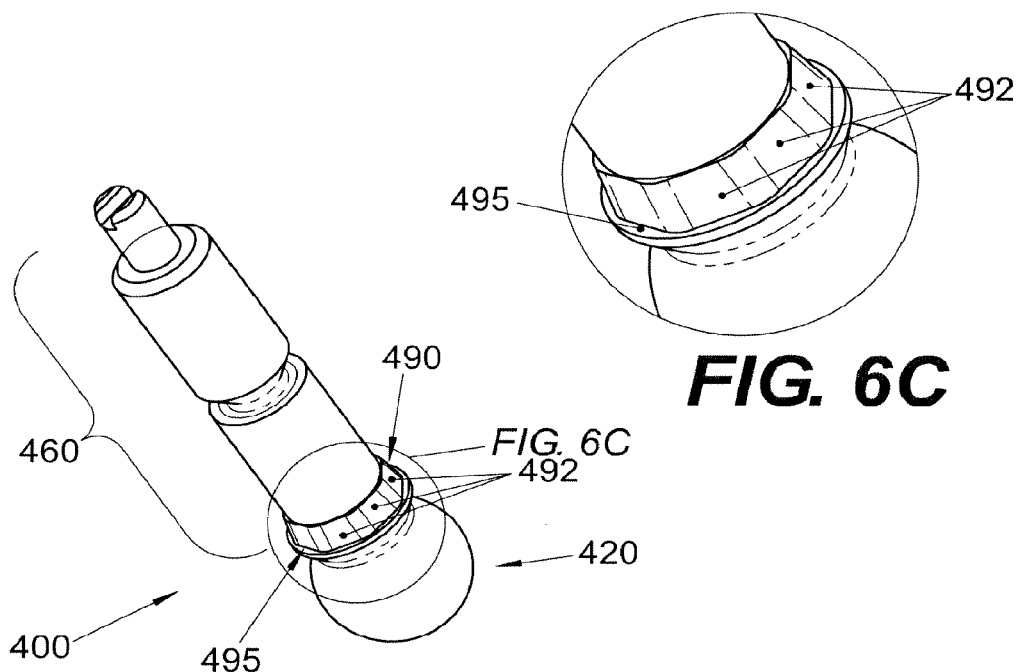
FIG. 6C
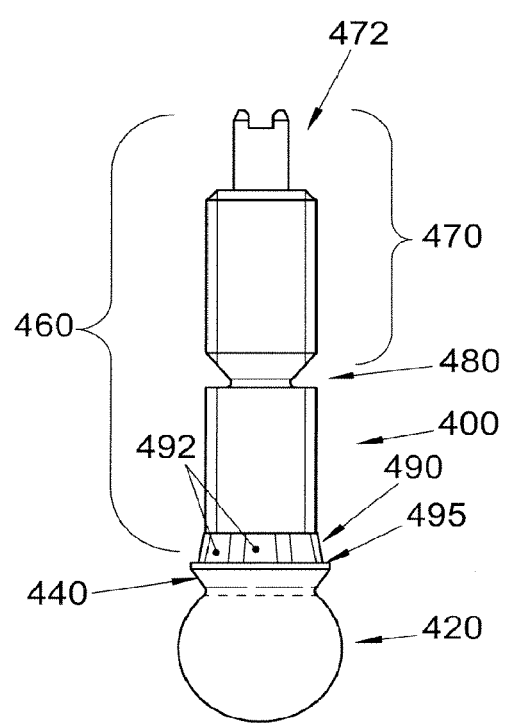
FIG. 6B
FIG. 6A

POLYAXIAL SCREW

CROSS-REFERENCE TO RELATED APPLICATIONS

This is a continuation application of U.S. patent application Ser. No. 11/538,524 filed on Oct. 4, 2006, and entitled "POLYAXIAL SCREW", which claims priority to U.S. Provisional Application No. 60/724,046 filed on Oct. 6, 2005, and entitled "POLYAXIAL SCREW," the contents of which are herein incorporated by reference in their entirety.

FIELD

The present invention relates to devices and methods for anchoring surgical implants to bony tissue. Specifically, the present invention pertains to polyaxial screws, which may be configured to attach to implantable rods.

BACKGROUND

Diseases of the spine cause significant morbidity. These diseases include abnormalities of the vertebrae, the intervertebral discs, the facet joints, and connective tissue around the spine. These abnormalities can be caused by a number of factors, including mechanical injury or degenerative disc disease. Such abnormalities can cause instability to the spine, vertebral misalignment, and abnormal motion between adjacent vertebrae. More severe disease may result in wear to the vertebral bony surfaces or cause nerve compression, and may ultimately produce severe pain. Further, these conditions are often chronic and progressive problems.

The treatments for spinal disorders may include long-term medical management or surgery. Medical management is generally directed at controlling the symptoms, such as pain, rather than correcting the underlying problems. For some patients this may require chronic use of pain medications, which may alter patient mental state or cause other negative side effects.

Another treatment option is surgery, which is often highly invasive and may significantly alter the spinal anatomy and function. For example, one surgical treatment for certain spinal conditions includes spinal fusion, whereby two or more vertebrae may be joined using bone grafts and/or synthetic implants. Fusion is irreversible and may significantly alter vertebral range-of-motion. Further, current surgical procedures are often only applicable to patients in a significantly progressed disease state.

Consequently, spinal surgeons have begun to develop more advanced surgical procedures and spinal stabilization and/or repair devices that are less invasive, may be reversible, and cause a less drastic alteration in the patient's normal anatomy and spinal function. These procedures may be used in an earlier stage of disease progression and, in some situations, may even stop or reverse disease progression.

Many devices and procedures that are designed to treat the spine or other body structures require bone-anchoring elements, which may include screws, pins, or nails. These bone-anchoring elements may connect one or more vertebrae with components of a treatment system. For example, pedicle screws are often used to connect spinal rods and/or plates to one or more vertebrae to facilitate fusion, correct a deformity, fix a fracture, and/or for a variety of other suitable treatment methods.

For some surgical procedures and implants, it is desirable to use a bone-anchoring element that can be implanted in a variety of configurations. For example, it is often desirable to use bone screws that can be fixed to bone at a range of suitable angles and still be properly connected with other components of an integrated treatment system.

Recently, spinal surgeons have begun to develop more dynamic treatment systems. Such systems may provide a certain degree of limited but controlled movement and may provide improved care for patients suffering from a variety of disorders including, for example, scoliosis and degenerative disc disease. These systems may benefit from improved bone-anchoring elements, including polyaxial screws.

SUMMARY

A first aspect of the present invention includes a bone-anchoring device. The bone-anchoring device may comprise a screw including a threaded shaft portion configured to engage bone tissue, and a head portion having a cup-shaped cavity. The device may further include a rod connector and a linking member, wherein the linking member includes a spherical head portion configured to engage the cup-shaped cavity of the head portion of the screw, a widened flange portion configured to engage the rod connector, and an elongate body extending from the widened flange portion and configured to extend through an opening in the rod connector.

A second aspect of the present invention includes a spinal treatment system. The spinal treatment system comprises a screw including a threaded shaft portion configured to engage bone tissue and a head portion having a cup-shaped cavity. The system further includes a linking member including a spherical head portion configured to engage the cup-shaped cavity of the head portion of the screw wherein the spherical head portion terminates at a widened flange portion. An elongate body extends from the widened flange portion. The system further includes a rod connector having an opening for receiving a spinal rod implant, and an opening for receiving the elongate body of the linking member.

It is to be understood that both the foregoing general description and the following detailed description are exemplary and explanatory only, and are not restrictive of the invention, as claimed.

The accompanying drawings, which are incorporated in and constitute a part of this specification, illustrate several embodiments of the invention and together with the description, serve to explain the principles of the invention.

Additional objects and advantages of the invention will be set forth in part in the description which follows or may be learned by practice of the invention. The objects and advantages of the invention will be realized and attained by means of the elements and combinations particularly pointed out in the appended claims.

BRIEF DESCRIPTION OF THE DRAWINGS

FIG. 6A provides a side view of a linking member of a bone-anchoring device, according to an exemplary disclosed embodiment.

FIG. 6B provides a perspective view of the linking member of FIG. 6A.

FIG. 6C shows an enlarged view of a portion of the linking member of FIG. 6B.

DESCRIPTION OF THE PREFERRED EMBODIMENTS

Figures 1A, 1B, 1C:
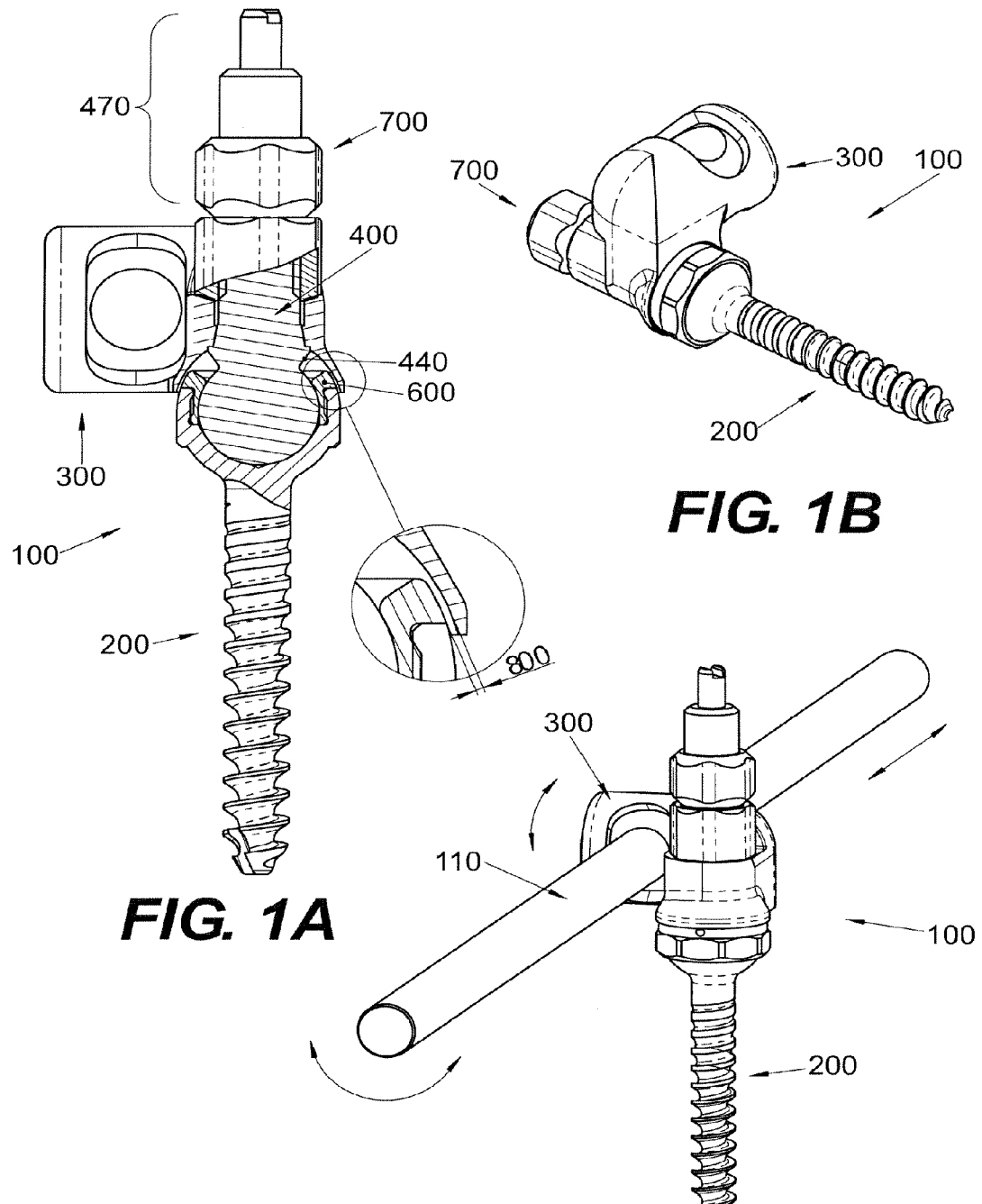
FIG. 1A illustrates a partial cutaway side view of a bone-anchoring device, according to an exemplary disclosed embodiment.
FIG. 1B illustrates a perspective view of the bone-anchoring device of FIG. 1A.
FIG. 1C illustrates a perspective view of the bone-anchoring device of FIG. 1A with an implantable rod.

FIGS. 1A-1C illustrate a bone-anchoring device 100, according to an exemplary disclosed embodiment. As shown, the bone-anchoring device 100 includes a screw 200, a rod connector 300, and a linking member 400. The screw 200 may be configured to engage bony tissue to secure the rod connector 300 to bone. In some embodiments, the screw 200 will be configured to engage a vertebra or a sacrum to secure an implantable rod 110 (as shown in FIG. 1C) to the vertebra or sacrum.

Figure 2:
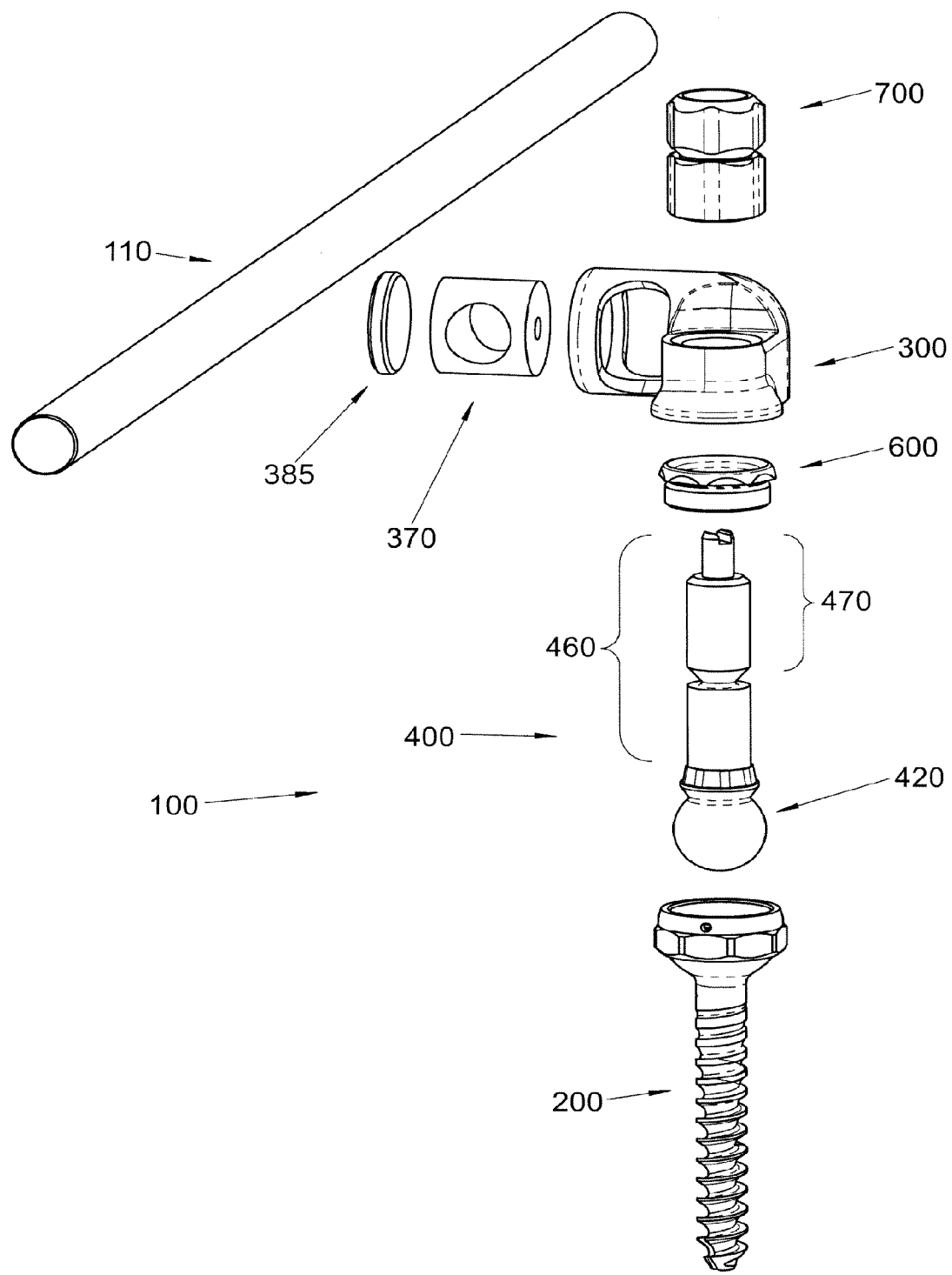
FIG. 2 illustrates an exploded view of the bone-anchoring device of FIG. 1C.

FIG. 2 illustrates the component parts of the bone-anchoring device 100, according to one exemplary embodiment. As noted, the bone-anchoring device 100 includes a screw 200, a rod connector 300, and a linking member 400. The screw 200 can be configured for insertion into bone tissue, while the linking member 400 can be configured to cooperate with the screw 200 in an angularly-adjustable relationship. In addition, the bone-anchoring device 100 may further include a locking collar 600 configured to secure the linking member 400 to the screw 200. The linking member 400 may be sized and configured to cooperate with a rod connector 300, as shown in FIGS. 1A-1C. A fastening member 700 may be provided to engage an end portion 470 of the linking member to secure the linking member 400 to the rod connector 300.

Figure 3B:
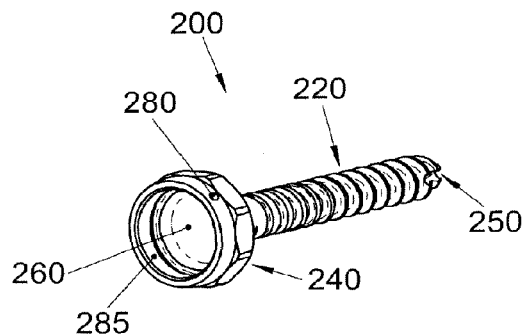
FIG. 3B provides a perspective view of the screw of FIG. 3A.
Figure 3A:
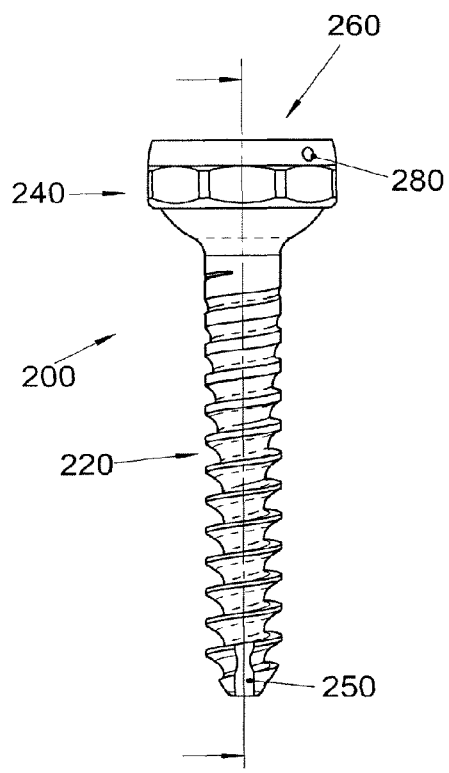
FIG. 3A provides a side view of a screw of a bone-anchoring device, according to an exemplary disclosed embodiment.
Figure 3C:
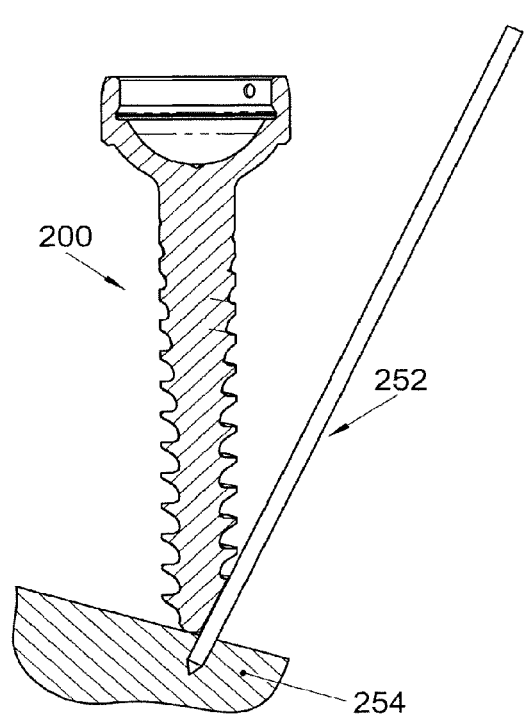
FIG. 3C provides a side view of the screw of FIG. 3A, according to an exemplary disclosed embodiment.

FIGS. 3A-3C illustrate the screw 200, according to an exemplary disclosed embodiment. The screw 200 can include a variety of suitable shapes, sizes, and/or materials. In one embodiment, the screw 200 can include a threaded shaft portion 220 and a head portion 240. The head portion 240 can further include a cup-shaped cavity 260 configured to engage the spherical head portion 420 of the linking member 400 (as shown in FIG. 1A).

The threaded shaft portion 220 can include any suitable material or thread design. For example, in one embodiment, the threaded shaft portion 220 will be produced from a material having biocompatibility with a tissue into which it is to be implanted. In another embodiment, the threaded shaft portion 220 will be produced from a material having a certain hardness, modulus of elasticity, or any other desired physical property. In addition, the thread size, shape, and number may be selected to securely fasten the screw 200 to bone.

Further, in some embodiments, the distal end of the threaded shaft portion 220 may include a groove 250, which may provide a seat for a guide wire 252, as shown in FIG. 3C. The guide wire 252 may facilitate placement of the screw 200 in a selected bone 254, such as a vertebral pedicle or other bone. For example, the guide wire 252 may be placed in a desired location through a small incision. The screw 200 may be positioned adjacent the bone 254 by sliding the groove 250 of the screw 200 along the length of the guide wire 252. The guide wire 252 may also allow verification of the position of the screw using radiographic means (i.e., with x-ray or fluoroscopy).

Figure 4A:
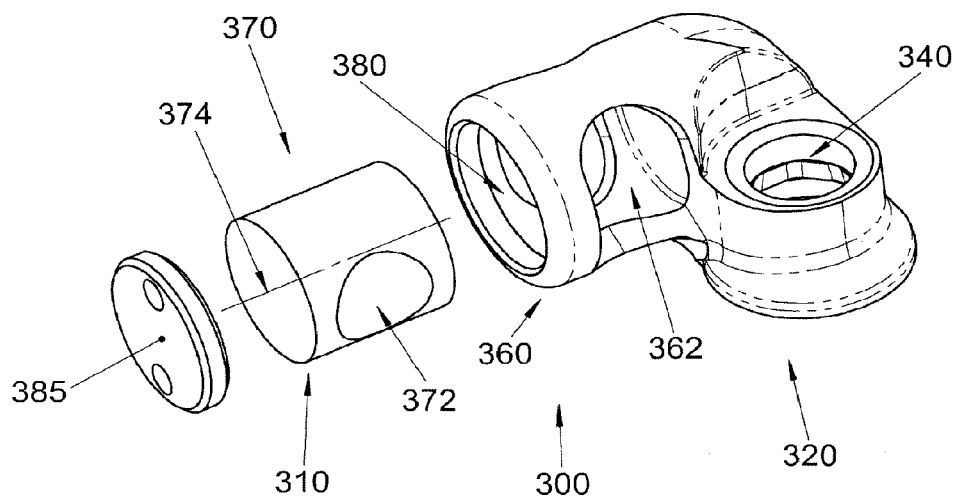
FIG. 4A illustrates an exploded view of a rod connector of a bone-anchoring device, according to an exemplary disclosed embodiment.
Figure 4C:
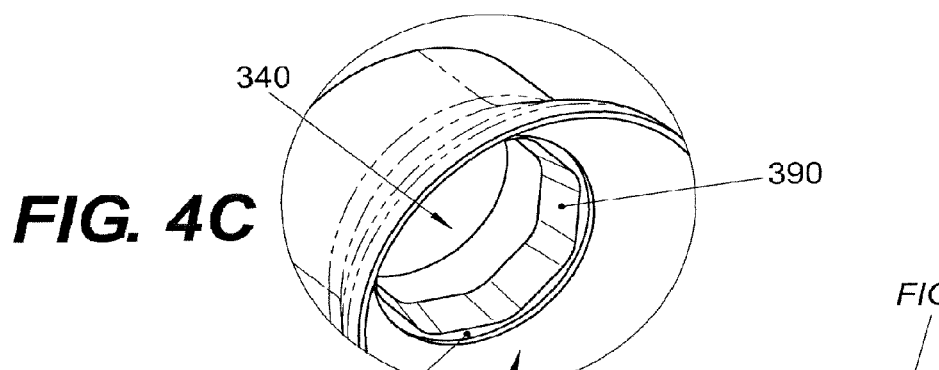
FIG. 4C shows an enlarged view of a portion of the rod connector of FIG. 4B.
Figure 4B:
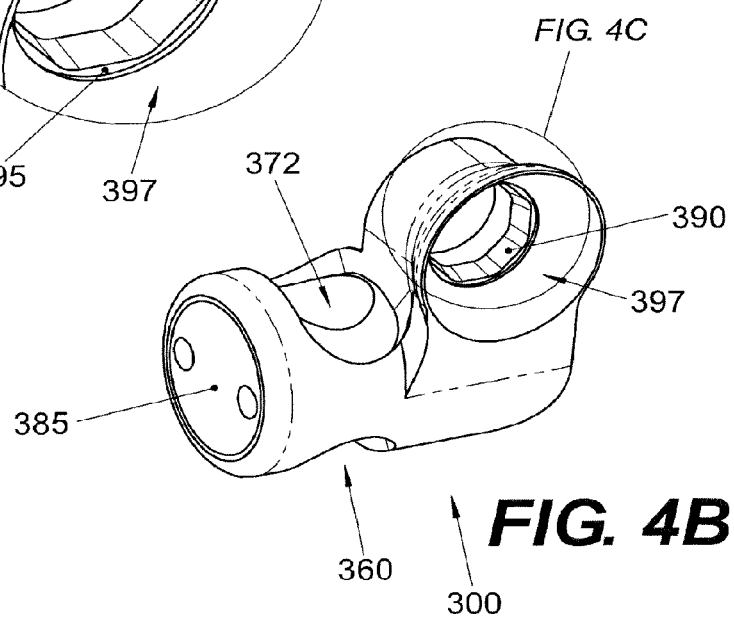
FIG. 4B illustrates a perspective view of the rod connector of FIG. 4A.

FIGS. 4A and 4B illustrate one embodiment for the rod connector 300. However, a number of suitable rod connectors may be used. In the embodiment shown in FIGS. 4A and 4B, the rod connector 300 can include a connector body 320 having a through hole 340 for receiving the linking member 400. The linking member through hole 340 can include a polygon-shaped internal surface portion 390 (shown in detail in FIG. 4C), which can form a complimentary connection with a polygon-shaped neck region 490 (as shown in FIGS. 6A and 6B) of linking member 400, thereby preventing rotation of the linking member 400 with respect to the rod connector 300. The rod connector 300 can further include a rod engaging section 360. The rod engaging section 360 can include a cylindrical bearing member 370. The cylindrical bearing member 370 can be disposed in a cavity 380 of the rod connector 300 (as shown in FIG. 4B), which may be closed with a rod connector cap 385. The cylindrical bearing member 370 can include a rod through hole 372 for receiving a spinal rod. Further, the cylindrical bearing member 370 may include a liner. The liner can be formed from any suitable polymeric, ceramic or metallic material in order to reduce friction or provide desirable wear characteristics. Suitable polymeric materials can include, for example, a polyethylene, such as ultra high molecular weight polyethylene (UHMWPE), or polyetheretherketone (PEEK).

In one embodiment, the cylindrical bearing member 370 may be configured to rotate about its longitudinal axis 374. Rotation of the cylindrical bearing member 370 can provide a certain degree of rotational mobility to a rod 110 placed within the through hole 372. The degree of mobility may be controlled by selecting the size of an opening 362 in rod engaging section 360. The larger the opening 362, the more clearance is provided for the rod 110 to be able to pivot with respect to the connector body 320. For example, in some embodiments, a rod 110 placed through a cylindrical member 370 within the connector body 320 may be configured to pivot up and down at an angle up to about 20.degree., up to about 30.degree., up to about 60.degree., up to about 90.degree., or up to about 120.degree. with respect to the connector body 320. In another embodiment, the cylindrical bearing member 370 may be securely connected to the rod engaging section 360 or form a single unit with the rod engaging section 360 to provide no rotational movement about its axis 374 if desired. In addition, the rod 110 may be configured to slide within the through hole 372, thereby providing translational and/or rotational movement of the rod 110 with respect to the rod connector 300.

Figure 5C:
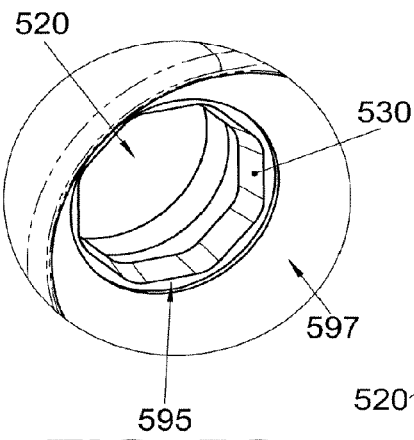
FIG. 5C shows an enlarged view of a portion of the rod connector of FIG. 5B.
Figure 5B:
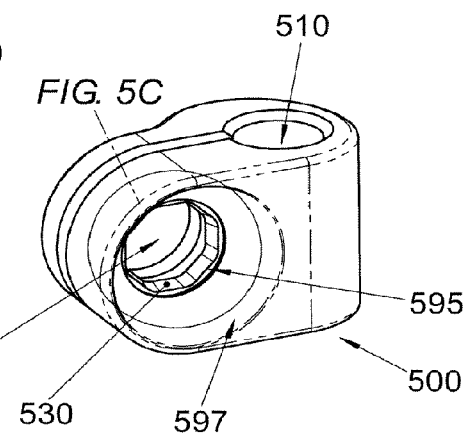
FIG. 5B provides a perspective view of the rod connector of FIG. 5A.
Figure 5A:
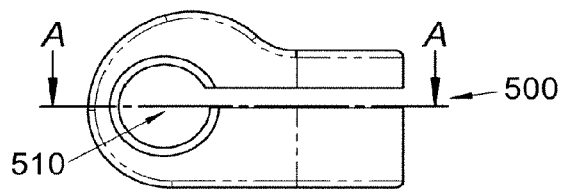
FIG. 5A provides a side view of another rod connector of a bone-anchoring device, according to an exemplary disclosed embodiment.

FIGS. 5A and 5B illustrate another type of rod connector 500. This rod connector 500 includes a C-shaped clamp with a rod receiving hole 510 and a linking member hole 520. This type of rod connector 500 may be selected when the rotational and/or translational movement of the cylindrical bearing member is not desired or needed. Like the rod connector 300 of FIGS. 4A and 4B, the linking member hole 520 can include a polygon-shaped internal surface portion 530 which can form a complimentary connection with a polygon-shaped neck region 490 (as shown in FIGS. 6A and 6B) of linking member 400, thereby preventing rotation of the linking member 400 with respect to the rod connector 500.

The rod connectors 300, 500 of FIGS. 4A-4C and 5A-5C may also include a semi-spherical recess portion 397, 597. As shown in FIG. 1A, the rod connector 300 may be configured such that, when assembled, the collar 600 and a portion of the screw head 240 may be positioned within the recess portion 397 of the rod connector 300. The size of the recess portion 397, 597 may be selected based on the size of the screw head 240 and linking member head 420 and may be configured to control the degree of rotational mobility of the linking member 400 with respect to the screw 200. Further, the rod connectors 300, 500 may include a rim 395, 595 adjacent to the semi-spherical recess portion 397, 597, as shown in FIGS. 4C and 5C.

Figure 8B:
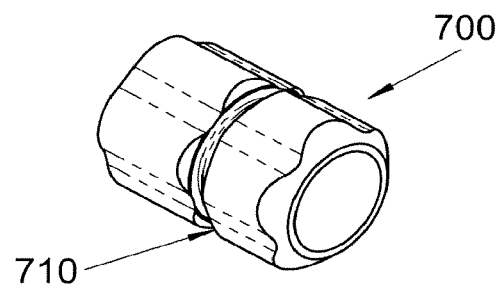
FIG. 8B provides a perspective view of the fastening member of FIG. 8A.
Figure 8A:
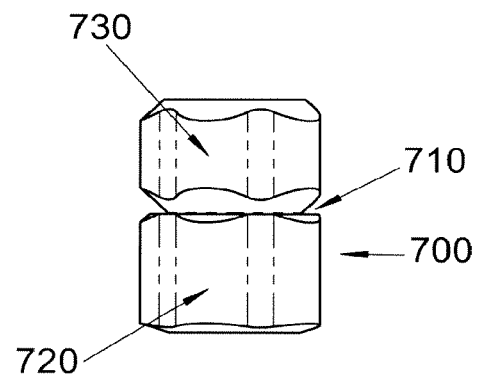
FIG. 8A provides a side view of a fastening member of a bone-anchoring device, according to an exemplary disclosed embodiment.

FIGS. 6A and 6B illustrate one embodiment of the linking member 400. The linking member 400 can include a spherical head portion 420, a widened flange 440 including a rim surface 495, and an elongate body 460 extending from the widened flange 440. To secure the linking member 400 and the rod connector 300, 500 together, the elongate body may be passed through the opening 340, 520 in the rod connector, and a fastening member 700 (as shown in FIGS. 8A and 8B) may be secured to the elongate body 460, thereby securing the rod connector 300 to the linking member 400. Further, as noted above, the linking member 400 may include a polygon-shaped neck region 490 configured to engage a complimentary surface of the linking member 300, 500 so as to prevent rotation. As shown in detail in FIG. 6C, the polygon-shaped neck region 490 may include a number of flat panels 492, which will form a desired surface configuration.

Figure 7B:
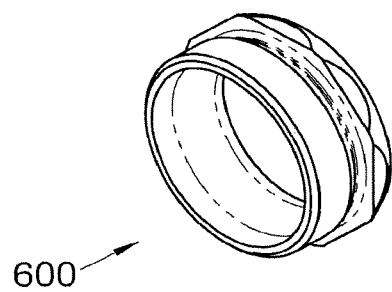
FIG. 7B provides a perspective view of the locking collar of FIG. 7A.
Figure 7A:
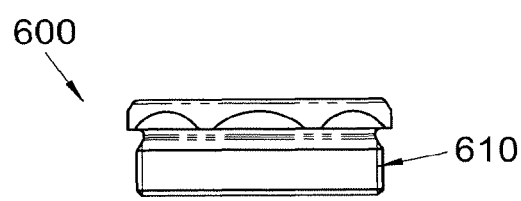
FIG. 7A provides a side view of a locking collar of a bone-anchoring device, according to an exemplary disclosed embodiment.

To assemble the bone-anchoring device 100, the linking member 400 is positioned against the screw 200 such that the spherical head portion 420 resides in the cup-shaped cavity 260 of the screw. To maintain the linking member 400 connected to the screw 200, the locking collar 600 (as shown in FIGS. 7A and 7B) can be placed over the linking member 400 and securely seated between the spherical head portion 420 of the linking member 400 and the cup-shaped cavity 260 of the screw 200 (as shown in FIG. 1A). It is contemplated, of course, that a partially assembled device may be provided to a surgeon for convenience (i.e. the screw 200 and the linking member 400 may be connected together by the locking collar 600 and provided to the surgeon as a unit, thereby eliminating the need for the previous assembly step), in order for the surgeon to be able to implant the screw 200 into a selected bone while the screw 200 is fastened to the linking member 400. Then, the rod connector 300 can be placed over the linking member 400 by inserting the linking member end portion 470 through the rod connector linking member hole 340. When the rod connector 300 has been properly positioned with respect to the linking member 400 and over the screw 200, the entire device 100 can be fully assembled by securing the fastening member 700 onto the linking member 400 and against the rod connector 300. It is understood that the linking member 400 may include a threaded portion along the length of its elongate body 460 to enable attachment to the fastening member 700.

As noted, the linking member 400 may include an elongate body 460, which may include an end portion 470. The elongate body end portion may further include a narrowed or tapered tip 472, which may be configured to be gripped or engaged by a surgeon's tool. Further, the elongate body 460 of the linking member 400 can include a thinner or scored section 480. The end portion 470 may extend a certain distance from the rod connector 300 during implantation, thereby facilitating manipulation of the linking member 400 and or connectors 300, 500 by a surgeon. Further, the thinner or scored section 480 may allow a surgeon to break off the end portion 470 of the elongate body 460 that is distal to the thinner or scored section 480. This will prevent excess protruding material after implantation, thereby reducing the foreign material left in a patient and preventing the end portion 470 from causing mechanical damage to surrounding tissue.

The linking member 400 may be produced from a number of different materials. The specific material may be selected based on desired physical properties, biocompatibility, cost, and/or any other suitable factor. For example, suitable materials may include various polymeric materials, ceramics, and/or metals. Such materials may include polyethylene, ultra high molecular weight polyethylene, PEEK, cobalt-chrome, and/or titanium or its alloys. In addition, the linking member 400 may be produced from multiple materials. For example, in one embodiment, the spherical head 420 may be produced from a hard, wear-resistant material, and the elongate body 460 may be produced from a softer material. Further, the end portion 470 may be produced from a material that can be relatively easily broken or cut at the thinner or scored section 480. In one embodiment, the linking member spherical head 420 will be produced from a polymeric material such as polyethylene or ultra-high molecular weight polyethylene. In other embodiments, the linking member spherical head 420 may be coated to reduce wear. For example, suitable surface coatings may include a variety of ceramic, composite, and/or polymeric materials.

FIGS. 7A and 7B illustrate a more detailed view of the locking collar 600, according to an exemplary disclosed embodiment. To secure the locking collar 600 to the spherical head portion 420 of the linking member 400 and the head 240 of the screw, the locking collar 600 may include a number of suitable fixation methods. For example, the locking collar 600 can be configured to form a friction fit connection, a snap-fit connection, a threaded connection, or any other suitable connection. In addition, the locking collar 600 may be removably or permanently fixed to the linking member 400 and the screw 200.

In one embodiment, the head 240 of the screw 200 may include a side hole 280. A fixation tool may be inserted through the side hole 280 to secure the locking collar 600 in place. For example, a small rod may be inserted through the side hole 280 with enough force to produce a small deformation in an inner surface 285 of the screw cavity and/or on a surface 610 of the locking collar. This deformation may prevent the locking collar 600 from being unscrewed (in the case of a threaded collar, the deformation would occur on the threads) or from sliding out (in the case of a friction fit collar). Alternatively, a pin or bolt may be inserted through the side hole 280 and left in place after assembly of the bone-anchoring device 100, thereby securing the locking collar 600 in place.

As noted, the linking member 400 can include a widened flange 440 terminating at a rim surface 495 adjacent the neck region 490. Upon passing the elongate body 460 through the opening 340, 520 in the rod connector 300, 500, the rim surface 495 engages the rim 395, 595 of the rod connector 300, 500. The abutment of the rim 395, 595 of the rod connector 300, 500 against the rim surface 495 of the linking member 400 serves to limit axial positioning of the two components relative to one another. In other words, the engagement of the rim 395, 595 of the rod connector 300, 500 with the rim surface of the linking member 400, as shown in FIG. 1A, prevents the rod connector 300, 500 from sliding down too far against the linking member 400 and screw 200, thereby allowing some control over the relative positions of the rod connector 300, 500, linking member 400 and screw 200. In addition, positioning the rim 395, 595 against the rim surface 495 may help stabilize the linking member 400 when subjected to physical stress while implanted within a patient.

FIGS. 8A and 8B illustrate the fastening member 700, according to an exemplary disclosed embodiment. The fastening member 700 can include a variety of suitable fastening member types. For example, in some embodiments, the elongate body 460 will include a threaded region over at least a portion of its length, and the fastening member 700 will include a nut that can be screwed onto the elongate body until it forms a tight connection with the rod connector 300, 500. In other embodiments, the fastening member 700 may be a press fit connector, friction fit connector, or any other suitable connector type. The rod connector 300, 500 may be configured with a recess cavity for receiving a portion of the fastening member 700.

In some embodiments, the fastening member 700 will include a narrowed section 710 connecting a lower half 720 and upper half 730. The narrowed section 710 may be configured to break when a certain torque is applied to the fastening member 700. For example, in some embodiments, a surgeon will tighten the fastening member 700 onto the linking member 400. When the fastening member 700 has been tightened sufficiently, the narrowed section 710 may break, thereby preventing excessive torque from being exerted on the device. Further, in some embodiments, the upper half 730 may include a widened internal diameter, which will allow the upper half 730 to be easily removed once the narrowed section 710 has been broken or cut.

Figure 9A:
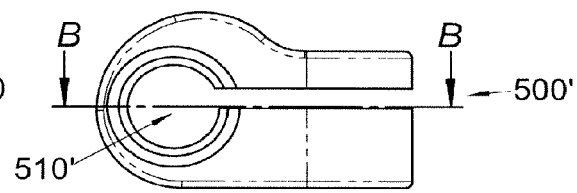
FIG. 9A provides a side view of yet another rod connector of a bone-anchoring device, according to an exemplary disclosed embodiment.
Figure 5D:
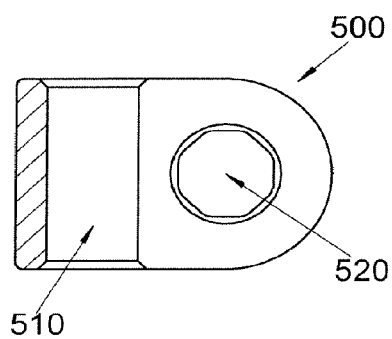
FIG. 5D shows a cross-sectional view of the rod connector of FIG. 5A along lines A-A.
Figure 9B:
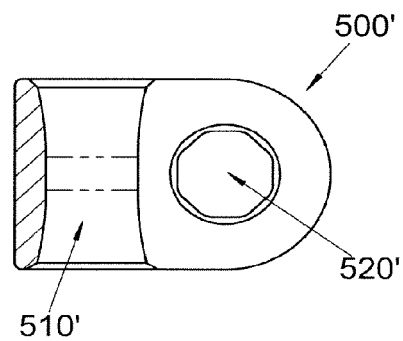
FIG. 9B provides a cross-sectional view of the rod connector of FIG. 9A along lines B-B.

As noted, the bone-anchoring device 100 of the present disclosure may be used to secure a variety of implantable rods to bone. For example, in one embodiment, the bone-anchoring device 100 may be used with a spinal treatment system. Suitable spinal treatment systems include mobile dynamic treatment systems for treatment of scoliosis and other spinal disorders. Examples of such mobile dynamic treatment systems are disclosed in U.S. Pat. No. 5,413,576 issued to Rivard on May 9, 1995 and U.S. Pat. No. 6,554,831 issued to Rivard on Apr. 29, 2003, both of which are herein incorporated by reference in their entirety. However, it should be noted that the bone-anchoring device 100 may be used with any suitable implantable rod. For instance, a straight or curved rod may be used with the bone-anchoring device 100 of the present invention. FIG. 5D illustrates a cross-sectional view of the rod connector 500 of FIG. 5A along lines A-A, showing a cylindrical rod receiving hole 510 configured for receiving a straight implantable rod 110. In another exemplary embodiment, the rod connector 500' may include a shaped rod receiving hole 510'. As shown in FIGS. 9A and 9B, the rod connector 500' may be similar in most respects to the rod connector 500 of FIGS. 5A-5D and can include a linking member hole 520', but can contain a curved rod receiving hole 510' in which the openings of the hole 510' extend in a slight flare. Such a configuration would enable a curved implantable rod to pass through the rod connector 500'. Of course, it is also possible to provide the cylindrical bearing member 370 of rod connector 300 with a similarly curved rod-receiving through hole in order to accommodate a curved rod, if desired, When used with dynamic spinal treatment systems, it may be desirable to maintain a certain degree of mobility between the treatment system components. For example, as noted previously, the rod connector 300 may include a cylindrical bearing member 370 configured to rotate along its axis 374, thereby providing a certain degree of rotation to a rod 110 disposed in the cylindrical body through hole 372. In addition, other types of sliding and rotational mobility may be provided.

In some embodiments, the rod 110 may be configured to be rotatably or slidably mobile with respect to the rod connector 300, 500 once inserted through a rod through hole 372, 510. Rotational movement of the rod 110 with respect to the rod connector 300, 500 will provide a certain degree of controlled mobility when implanted in a patient. Furthermore, sliding mobility of the rod connector 300, 500 can allow some degree of flexion and/or extension, while also allowing continued elongation of the spine. As noted by Rivard, this may be important when the bone-anchoring device 100 is implanted in a juvenile patient who will continue to grow.

It should also be noted that in some embodiments, rod connectors 300, 500 may be configured to prevent movement in one or more degrees of freedom. For example, in some embodiments, rod connector 500 may be configured to prevent translational or sliding movement of a rod 110. Such rod connectors 500, which may limit translational or sliding movement, may be included as part of a dynamic treatment system, which may include combinations of sliding and fixed connectors 300, 500.

Finally, in some embodiments, the linking member spherical head 420 may rotate with respect to the axis of the screw 200 after assembly. In some embodiments, there may be a gap 800 (as shown in FIG. 1A) between the locking collar 600 and/or screw head 240 and the semi-spherical recess portion 397, 597 of the rod connector 300, 500. This gap 800 can allow some freedom of movement, or rotation, of the spherical head 420 of the linking member 400 within the cup-shaped cavity 260 of the screw 200.

The rotational movement of the linking member spherical head 420 with respect to the screw 200 will provide a number of advantages. For example, the screw 200 can be implanted at a variety of suitable angles in a patient's bone while still allowing appropriate engagement of the linking member 400 with the screw cup-shaped cavity 260. In addition, in some embodiments, continued rotational mobility of the linking member 400 with respect to the screw 200 will provide controlled dynamic movement, which may be desired for some implantable devices.

In other embodiments, continued mobility of the implant components may not be desired. For example, for some applications, it may be desirable to rigidly secure an implant rod 110. In these embodiments, the size and shape of the screw head 240, linking member spherical head 420, and rod connector 300, 500 may be selected to prevent movement after implantation. Further, as noted previously, a rod connector 500 may be selected that does not include a cylindrical bearing member 370, thereby preventing another type of rotational movement of the rod 110 with respect to the rod connector 500.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a spine, comprising:
   providing a spinal treatment system including:
      a screw having a threaded shaft portion configured to engage bone tissue, and a head portion having a cup shaped cavity;
      a linking member having a spherical head portion configured to engage the cup-shaped cavity of the head of the screw, the spherical head portion terminating at a widened flange portion that extends from the spherical head portion to form a rim surface configured to engage a rod connector, and an elongate body extending from the widened flange portion;
      a rod connector having a first opening for receiving a spinal rod implant, a second opening for receiving the elongate body of the linking member, and a recess portion configured to engage at least a portion of the spherical head portion of the linking member; and
      a spinal rod implant configured for placement through the first opening of the rod connector;
   anchoring the screw to a vertebra of the spine;
   assembling the spinal rod implant, rod connector and linking member to the screw; and
   securing the rod connector to another vertebra of the spine to treat the spine.

2. The method of claim 1, wherein the system includes a cylindrical body configured for placement within a cavity of the rod connector, and further including the step of placing the spinal rod implant through the cylindrical body.

3. The method of claim 2, wherein the cylindrical body includes a liner, and the spinal rod implant is placed through the liner.

4. The method of claim 3, wherein the liner comprises a polymeric, ceramic or metallic material.

5. The method of claim 4, wherein the polymeric material is polyethylene, ultra high molecular weight polyethylene (UHMWPE), or polyetheretherketone (PEEK).

6. The method of claim 2, wherein the cylindrical body is rotatably adjustable with respect to at least one axis of the rod connector.

7. The method of claim 1, wherein the rod connector includes a recess for receiving a portion of the head portion of the screw.

8. The method of claim 1, wherein the system includes a locking collar configured to secure the spherical head portion within the cup-shaped cavity of the head portion.

9. The method of claim 1, wherein the system includes a fastening member for engaging the elongate body of the linking member, and further including the step of securing the fastening member to the elongate body of the linking member.

10. The method of claim 9, wherein the fastening member and elongate body of the linking member both include a break-away portion, and further including the step of breaking away a portion of the fastening member and elongate body of the linking member.

11. The method of claim 9, wherein the rod connector includes a recess for receiving a portion of the fastening member.

12. The method of claim 1, wherein the system is dynamic, and the rod connector and the linking member are rotationally moveable with respect to an axis of the screw after assembly.

13. The method of claim 1, wherein the system is rigid, and the rod connector and the linking member are rigidly fixed with respect to the screw after assembly.

14. The method of claim 1, wherein the system is dynamic, and the spinal rod implant is slidable or rotatable with respect to the rod connector after assembly.

15. The method of claim 1, wherein the spinal rod implant is a straight rod implant.

16. The method of claim 1, wherein the spinal rod implant is a curved rod implant.

* * * * *